United States Patent [19]

McCullough

[11] Patent Number: 4,554,250

[45] Date of Patent: Nov. 19, 1985

[54] METHOD OF INCREASED PRODUCTION OF PENICILLIN ACYLASE AND PLASMID EMPLOYED THEREIN

[75] Inventor: John E. McCullough, Whitehouse Station, N.J.

[73] Assignee: E. R. Squibb & Sons, Inc., Princeton, N.J.

[21] Appl. No.: 509,501

[22] Filed: Jun. 30, 1983

[51] Int. Cl.[4] .................... C12N 15/00; C12N 1/20; C12N 9/86; C12N 1/00

[52] U.S. Cl. .................... 435/172.3; 435/253; 435/231; 435/317; 435/837; 935/29; 935/60; 935/74; 935/14

[58] Field of Search ................. 435/172, 317, 44, 253, 435/231, 837, 172.3

[56] References Cited

U.S. PATENT DOCUMENTS 3,446,705  5/1969  Heuser et al. .................... 435/44

OTHER PUBLICATIONS

Clarke et al, Methods in Enzymology, vol. 68, pp. 396–408, (1979).

Cole et al, Methods in Enzymology, vol. XLIII, pp. 698–721, (1975).

Lovett, P. S. et al., "Expression of a Foreign Procargotic Gene in *Bacillus subtilis* in Genetic Engineering of Microorganisms for Chemicals", (eds. Hollaender, A. et al), 51–59, (Plenum Press, New York, 1982).

Brown and Carlton, "Plasmid Mediated Transformation in *Bacillus megaterium*," J. Bact. 142, 508–512, (1980).

Keggins et al., "Molecular Cloning of Genetically Active Fragments of Bacillus DNA in *Bacillus subtilis* and Properties of Vector Plasmid pUB110," *Proc. Nat. Acad. Sci. USA* 75, (1978).

*Primary Examiner*—Alvin E. Tanenholtz
*Attorney, Agent, or Firm*—Lawrence S. Levinson; Burton Rodney

[57] ABSTRACT

A method is provided for enhancing penicillin acylase production wherein a *Bacillus subtilis* plasmid containing an insert of a chromosomal DNA fragment of *Bacillus megaterium* which includes the appropriate gene for enhancing penicillin acylase production is cloned into *Bacillus megaterium* and the *Bacillus megaterium* containing the above plasmid is employed in the production of penicillin acylase.

A plasmid method for forming same and host plasmid combination which are useful in the above method are also provided.

5 Claims, 1 Drawing Figure

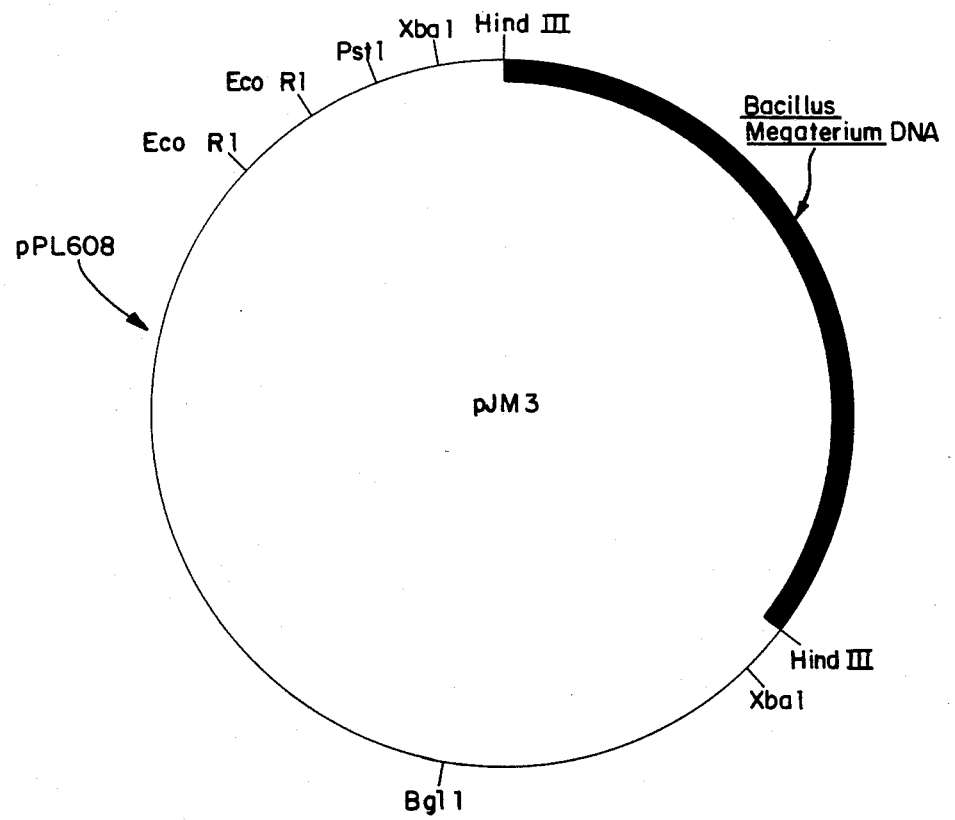

METHOD OF INCREASED PRODUCTION OF PENICILLIN ACYLASE AND PLASMID EMPLOYED THEREIN

FIELD OF THE INVENTION

The present invention relates to a method for increasing production of penicillin acylase and to improved strains of *Bacillus megaterium* useful in the production of penicillin acylase.

BACKGROUND OF THE INVENTION

Penicillin acylases are enzymes which are produced by many different microorganisms including both bacteria and fungi as disclosed by Claridge et al., "Bacterial Penicillin Amidase." *Nature* 187, 237-238 (1960), Rolinson et al., "Formation of 6-Aminopenicillanic Acid from Penicillin by Enzymatic Hydrolysis." *Nature* 187, 236-237 (1960), and Sakaguchi et al., "A Preliminary Report on a New Enzyme Penicillin Amidase," *J. Agr. Chem. Soc. Japan,* 23, 411 (1950). These enzymes catalyze the hydrolysis of the phenylacetic acid side chain from benzyl penicillin to give 6-aminopenicillanic acid which is used commercially in the production of semisynthetic penicillins.

Bacillus strains, such as *Bacillus megaterium* ATCC 14945 are highly productive for penicillin acylase. Derivatives of *Bacillus megaterium* ATCC 14945 have been obtained using conventional mutagenesis and screening techniques which produce much higher industrial penicillin acylase yields than does ATCC 14945. However, techniques for producing penicillin acylase in even higher yields are still highly sought after.

Recombinant DNA technology has been used with success by many researchers in increasing the production of products specified by a single gene through the insertion of that gene on multi-copy plasmids in genetically well understood host organisms such as *E. Coli, S. cerevisiae* or *B. subtilis*. However, until now, no one has applied recombinant DNA technology to *Bacillus megaterium* to further improve industrial penicillin acylase yields.

BRIEF STATEMENT OF THE INVENTION

In accordance with the present invention, a method is provided whereby through the use of recombinant DNA technology improved yields of penicillin acylase are obtained which yields are substantially greater than hithertofore obtained using conventional mutagenesis and screening techniques. The method of the invention for improving yields of penicillin acylase comprises isolating a selected chromosomal DNA fragment from *Bacillus megaterium* which fragment contains the appropriate gene for enhancing penicillin acylase production, inserting such DNA fragment in a multi-copy vector, which replicates in gram positive bacteria, and then transforming the resulting multi-copy vector containing said DNA fragment into a host organism that already is known to synthesize penicillin acylase, namely *Bacillus megaterium,* to produce a *Bacillus megaterium* having enhanced penicillin acylase productivity.

Further, in accordance with the present invention, there is provided a cloning vector plasmid (obtained from *Bacillus subtilis*) namely pPL608, which includes as an insert therein a selected chromosomal DNA fragment from *Bacillus megaterium,* which fragment is a 1 kb to 10 kb chromosomal DNA fragment, and preferably a 2.7 kb chromosomal DNA fragment, which fragment includes the appropriate gene to enhance penicillin acylase production; the above preferred plasmid is referred to as plasmid pJM3.

In addition, in accordance with the present invention, there is provided a new strain of *Bacillus megaterium,* namely SC3593 (pJM3), having enhanced acylase productivity which includes the cloning vector or plasmid pPL608 containing the 2.7 kb chromosomal DNA fragment.

DETAILED DESCRIPTION OF THE INVENTION

The plasmid pJM3 is formed of a *Bacillus subtilis* plasmid pPL608 (Lovett, P.S. et al., "Expression of a Foreign Procargotic Gene in *Bacillus subtilis* in Genetic Engineering of Microorganisms for Chemicals" (eds. Hollaender, A. et al.) 51-59 (Plenum Press, New York, 1982)) containing a Hind III fragment of *Bacillus megaterium* DNA (2.7 kb) inserted at its unique Hind III site.

Within this Hind III fragment of *Bacillus megaterium* chromosomal DNA is a gene which can be inserted into any *Bacillus megaterium* strain having the ability to synthesize penicillin acylase, using the transformation procedure described by Brown and Carlton "Plasmid Mediated Transformation in *Bacillus megaterium*." J. Bact. 142. 508-512 (1980). Such *Bacillus megaterium* strains containing pJM3 produce higher titers of penicillin acylase than identical strains not containing the plasmid.

Where the chromosomal DNA fragment selected from *Bacillus megaterium* is a 1 kb to 10 kb chromosomal DNA fragment other than a 2.7 kg DNA fragment, then a restriction enzyme other than Hind III is employed, namely, MboII, HpaII, HaeIII or EcoRI is employed. The fragment of 1 kb-10 kb DNA (other than the 2.7 kb fragment) will include the appropriate gene for penicillin acylase production and may be inserted in *Bacillus subtilis* following procedures described herein to form an appropriate plasmid. The so-formed plasmid may be cloned into *Bacillus megaterium* using procedures described herein.

REFERENCE TO THE DRAWING

Restriction enzyme map for pJM3. The inserted *Bacillus megaterium* segment is located between the two Hind III sites.

THE MICROORGANISMS AND PLASMIDS

The following microorganisms are available from the permanent collection of the American Type Culture Collection, 12301 Parklawn Drive. Rockville, Maryland 20852.

*Bacillus megaterium* SC3593, ATCC 14945
*Bacillus megaterium* SC3593, ATCC 14945 (pJM3)—ATCC 39383

The latter deposit is available to the public upon the grant of a patent to the assignee, E. R. Squibb & Sons, Inc., disclosing them. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

The following example represents preferred embodiments of the present invention.

EXAMPLE

A plasmid (pJMI) containing a chromosomal DNA fragment from *Bacillus megaterium* (SC3593, ATCC 14945) was prepared as described below.

The expression vector pPL608 (*Bacillus subtilis*) (Lovett, P.S. et al., "Expression of a Foreign Procaryotic Gene in Bacillus Subtilis in Genetic Engineering of Microorganism for Chemicals" (eds. Hollaeder, A et al.) 51–59 (Plenum Press, New York, 1982)) was used. This vector confers resistance to both neomycin and chloramphenicol to its host and has a Hind III (restriction enzyme) insertional inactivation site in the chloramphenicol acetyl transferase gene (CAT).

A small plasmid library was constructed by inserting *Bacillus megaterium* Hind III chromosomal fragments at this Hind III site. This was done by cleaving both pPL608 and *Bacillus megaterium* DNA with the restriction enzyme Hind III. The DNA was mixed and re-circulated with polynucleotide ligase. This DNA was introduced into *Bacillus subtilis* using the transformation procedure of Keggins et al. "Molecular cloning of genetically active fragments of Bacillus DNA in *Bacillus subtilis* and properties of vector plasmid pUB110." *Proc. Nat. Acad. Sci. USA* 75, (1978). 1500 *Bacillus subtilis* isolates were obtained which were resistant to neomycin but sensitive to chloramphenicol.

The average size of the inserts in the library of *Bacillus megaterium* (3593) Hind III fragments was 3.2 kb as judged by size measurements of inserts in a random sample of 20 of the plasmids.

*Bacillus megaterium* strain SC 3593 (pJM3) containing the plasmid (pJM3) was selected as described below.

Plasmid DNA from the library was introduced into *Bacillus megaterium* SC3593 by transformation. The transformation method used was the same as the *Bacillus megaterium* transformation method developed by Brown and Carton, "Plasmid Mediated Transformation in *Bacillus megaterium*", J. Bact. 142, 508–512 (1980) with the following modifications. A lysozyme concentration of 1 mg/ml was required for protoplasting. The protoplasts were allowed to regenerate on DM-3 plates without antibiotic selection and transformed cells were selected by replica plating onto antibiotic-containing media (neomycin at 2.5 μg/ml).

The transformants were screened using the rapid filter paper plate screen described by Szweczuk et al., "Colorimetric assay of penicillin amidase activity using phenylacetyl, aminobenzoic acid as substrate" *Analytical Biochem.*, 103, 166–169 (1980).

The following modifications were made in their method for the filter paper colony assay. The filter papers were dried at 65° for seven minutes after they were removed from the plates. The concentrations of both the sodium nitrite and H-acid sprays were increased tenfold. To assay the high penicillin acylase producers, the substrate concentration was halved and phenylacetic acid was added to a 2% concentration to the substrate buffer. Colonies grown on tryptose blood agar base (TBAB, Difco) plates could be assayed using this method.

One *Bacillus megaterium* transformant containing a plasmid gave a more intense spot in this test than did the untransformed SC3593 in repeated tests.

A 7.7 kb plasmid (pJM3) was isolated from this strain (SC3593 (pJM3). Digestion of this plasmid with Hind III and electrophoresis through a 1% agarose gel revealed that the plasmid contained a fragment identical in size to pPL608 plus an additional 2.7 kb fragment.

The *Bacillus megaterium* strain SC3593 (pJMI) was tested for penicillin acylase production as follows.

Using a sterile loop, *Bacillus megaterium* cells from slants incubated 24 hours at 30° were inoculated into 500 ml Erlenmeyer flasks with 100 ml of medium containing enzyme hydrolyzed casein (4.0% w/v) and cornsteep liquor (1.0% w/v) and pH adjusted to 6.8. These flasks were shaken on a rotary shaker (280 rpm) for 24 hours at 30°. Five ml were removed and used to inoculate 500 ml Erlenmeyer flasks containing 100 of medium containing enzyme hydrolyzed casein (3.0%) and yeast extract (0.5%) and pH adjusted to 6.8. Phenyl acetic acid was added to this medium at a final concentration of 0.2% immediately prior to innoculation. These flasks were harvested and assayed for penicillin acylase after 24 hour and 42 hour incubation at 30° on a rotary shaker (280 rpm).

The shaken flask broths were assayed for penicillin acylase by the photometric assay using phenylacetyl-aminobenzoic acid as a chromogenic substrate described by Szweczuk et al., "Colormetric Assay of Penicillin Amidase Activity Using Phenylacetyl. Aminobenzoic Acid as Substrate," *Analytical Biochem.*, 103, 166–169 (1980).

The results of shaken flask tests are set out in the following table.

TABLE

Shaken flask tests of *B. megaterium* SC3593 strains for acylase productivity.

| Strain SC | 24-Hr.* Titer | 42-Hr.* Titer | 42-Hr.* Average | Percent Increase |
|---|---|---|---|---|
| 3593 | 2.7 | 3.8 | 3.6 | |
| 3593 | 3.1 | 3.4 | | |
| 3593(pJM3) | 3.4 | 4.4 | 4.3 | 20%[a] |
| 3593(pJM3) | 3.5 | 4.2 | | |

[a]Percent increase over 3593.
*Units of activity are arbitrary.

The results of shaken flask tests as seen in the above Table show that the penicillin acylase yield of SC3593 (pJM3) is 20% higher than the yield of SC3593. This agreed with the qualitative agar plate assay.

What is claimed is:

1. Plasmid PJM3 characterized in that it has the entire nucleotide sequence of *Bacillus subtilis* plasmid pPL608 and an insert which is a 2.7 kb chromosomal DNA fragment of *Bacillus megaterium* ATCC 14945 containing the gene for penicillin acylase production which is inserted at the Hind III site of pPL608.

2. *Bacillus megaterium* SC3593 (pJM3) having the ATCC deposit accession number 39383.

3. A process for forming the *Bacillus megaterium* defined in claim 2 which comprises inserting plasmid pJM3 into *Bacillus megaterium* SC3593 (ATCC 14945) by transformation.

4. A process for preparing plasmid pJM3 as defined in claim 1, which comprises
   (a) linearizing plasmid pPL608 with Hind III to obtain linear plasmid DNA,
   (b) obtaining a 2.7 kb chromosomal DNA fragment from *Bacillus megaterium* ATCC 14945 containing the gene for penicillin acylase by digesting said chromosomal DNA with Hind III and (c) ligating said digested linear plasmid DNA from pPL608 and said digested chromosomal DNA from *Bacillus megaterium* ATCC 14945 to obtain said plasmid.

5. A process for improving penicillin acylse production which comprises forming plasmid pJM3 as defined in claim 1, inserting said plasmid into *Bacillus megaterium* ATCC 14945 to form *Bacillus megaterium* ATCC 14945 (pJM3) and employing said *Bacillus megaterium* ATCC 14945 (pJM3) in the production of penicillin acylase.

* * * * *